US006288033B1

(12) United States Patent
Leung

(10) Patent No.: US 6,288,033 B1
(45) Date of Patent: Sep. 11, 2001

(54) TREATMENT OF HEPATITIS B INFECTION WITH THYMOSIN ALPHA 1 IN COMBINATION WITH LAMIVUDINE OR IN COMBINATION WITH LAMIVUDINE AND FAMCICLOVIR

(75) Inventor: Ying-Kit Leung, Hong Kong (CN)

(73) Assignee: SciClone Pharmaceuticals, Inc., San Mateo, CA (US)

( * ) Notice: Subject to any disclaimer, the term of this patent is extended or adjusted under 35 U.S.C. 154(b) by 0 days.

(21) Appl. No.: 09/168,869

(22) Filed: Oct. 9, 1998

Related U.S. Application Data
(60) Provisional application No. 60/101,771, filed on Sep. 25, 1998.

(51) Int. Cl.[7] .......................... A61K 38/12; A61K 38/16; A61K 38/22
(52) U.S. Cl. .................. 514/12; 514/9; 530/399
(58) Field of Search ........................... 514/12, 9; 530/399

(56) References Cited

U.S. PATENT DOCUMENTS

| 5,308,833 | 5/1994 | Scharschmidt | 514/12 |
| 5,939,423 | * 8/1999 | Karlin et al. | 514/262 |

FOREIGN PATENT DOCUMENTS

| 0388049 | 9/1990 | (EP) | A61K/31/52 |
| 9401125 | 1/1994 | (WO) | A61K/37/02 |
| 9846256 | 10/1998 | (WO) | A61K/38/22 |

OTHER PUBLICATIONS

Leung, Y.K. et al., "Treatment of chronic hepatitis B using thymosin alpha 1 and a combination of two nucleoside analogs, lamivudine and famciclovir." *Hepatology*, vol. 28, No. 4, part 2, Nov. 6–10, 1998, p. 216A.
Naylor, P.H., "Zadaxin (thymosin.alpha.1) for the treatment of viral hepatitis." *Expert Opinion on Investigational Drugs*, 8/3 (281–287) vol. 8, No. 3, Mar. 1999, pp. 281–287.
Lai Ching–Lung et al., "A one-year trial of lamivudine for chronic hepatitis B" *New England Journal of Medicine*, vol. 339, No. 2 Jul. 1998, pp. 61–68.
Hong, J.H. et al. "Current status of anti–HBV chemotherapy" *Archives of Pharmacal Research*, vol. 21, No. 2, Apr. 1998, pp. 89–105.
Bartholomeusz, A., et al., "Mutations in the hepatitis B virus polymerase gene that are associated with resistance to famciclovir and lamivudine" *International Antiviral News*, vol. 5, No. 8, 1997, pp. 123–124.
Lai et al. "Antiviral Treatment for Chronic Hepatitis B" *Hong Kong Medical Journal*, vol. 3, No. 3, Sep. 1997, pp. 289–296.
Lai et al. BIOSIS abstract, Accession No. 1998:29755. Article published in Hong Kong Medical Journal vol. 3 (3), pp. 289–296. (9/1997). Abstract only.*

Liaw, Y–F. Current therapeutic trends in therapy for chronic viral hepatitis. J. Gastroenterology and Hepatology, 12 (9–10), pp. S346–S353. (1997).*
Doctors Guide to Medical and Other News, "Famvir is Safe and Effective for Treatment of Hepatitis B", Chicago, Nov. 11, 1996.
ALF Progress Index, Hepatitis B Drug Studies, "Two 'Promising' Drugs Under Study for Hepatitis B", American Liver Foundation, 1425 Pompton Avenue, Cedar Grove, NJ 07009, (Mar. 1997).
"Chronic Hepatitis B Virus Infection Phase I–II Treatment Study", Protocol: 95–I–0062, Dr. Adriana Marques, Building 10, Room IIN228, 10 Center Dr MSC 1888, Bethesda, MD 20892, (Mar. 1997).
TT Aye. Al Bartholomeusz et al., "Hepatitis B virus polymerase mutations during famciclovir therapy in patients following liver transplantation", VIDRL Publications, (1996).
TT Aye. Al Bartholomeusz et al., "Hepatitis B virus polymerase mutations induced by famciclovir therapy", VIDRL Publications, (Sep.1996).
CenterWatch Study Information (10), Trial Information, Summary: Study of an investigational treatment for HbeAg+ chronic hepatitis B, Libby Behler/Ingrid Crause, Study Contacts, University of Michigan, GCRC, 3912 Taubman Center, 1500 E. Medical Center Drive, Ann Arbor, MI 48109–0362, (Mar. 1997).
Penciclovir/famciclovir (SmithKline–Beecham) shows promise against duck HBV and was used successfully for "compassionate" reasons with two patients in Australia) reported at the International Antiviral Meeting, Charleston. S.C. Mar. 1994).
Doctors Guide to Medical and Other News, "Famvir is Safe and Effective for Treatment of Hepatitis B", Nov. 11, 1996.
De Man et al., "New Developments in Antiviral Therapy for Chronic Hepatitis B Infection", Scand. J. Gastroenterol. 30, Suppl. 212, 100–104 (1997).
Andreone et al., Hepatology 24 (4), 774–777. (Abstract) (1996).
Database Investext, 97:519492 Report No: 190487, SciClone Pharmaceuticals, Inc., Company Report, 2 pages. (May 1997).
Database Investext, Report No. 1293001, Biotechnology–Industry Report, 2 pages (Jan. 1993).
Marinos et al., Hepatology, 24, 991–995 (Abstract) (1996).

* cited by examiner

*Primary Examiner*—Michael P. Woodward
*Assistant Examiner*—Marjorie A. Moran
(74) *Attorney, Agent, or Firm*—Rothwell Figg Ernst & Manbeck

(57) ABSTRACT

A method of treatment of hepatitis B virus (HBV) infection in a patient by administering to the patient a drug regimen including an antiviral-effective amount of thymosin alpha 1 (Tα1), an antiviral-effective amount of lamivudine, and optionally an antiviral-effective amount of famciclovir is disclosed.

17 Claims, No Drawings

TREATMENT OF HEPATITIS B INFECTION WITH THYMOSIN ALPHA 1 IN COMBINATION WITH LAMIVUDINE OR IN COMBINATION WITH LAMIVUDINE AND FAMCICLOVIR

This application claims benefit of Provisional No. 60/101,771 filed Sep. 25, 1998.

FIELD OF THE INVENTION

The present invention relates to the field of hepatitis B treatment.

BACKGROUND OF THE INVENTION

Chronic hepatitis B virus (HBV) infection is a serious global health problem affecting around 300 million individuals. Among them, approximately seventy-five percent are believed to be Asian. It also is estimated that 25–40% of these HBV carriers will die of cirrhosis or hepatocellular carcinoma.

In contrast to the course of the disease in Caucasians, the natural history of chronic HBV infection in Asians is characterized by an initial active viral replicative state with minimal liver damage (immune tolerance phase), followed by an active immune clearance phase with chronic active hepatitis, and later an inactive HBV non-replicative phase with the development of cirrhosis that may be complicated by hepatocellular carcinoma (HCC). In addition, a fourth phase, characterized by viremia and chronic active hepatitis in the absence of HBE antigenaemia may follow. The main aim of current treatment is to suppress HBV replication before there is any significant irreversible liver disease. As most of the liver damage occurs during the immune clearance phase (when HBV replication is being suppressed spontaneously), it would be ideal to suppress HBV replication in an earlier phase (immune tolerant phase).

So far, therapeutic trials have mainly been directed toward utilization of anti-viral agents, immunomodulators, immunosuppressives or certain specific combinations of these. At present, interferon-alpha is the only therapeutic approach that has had regulatory approval in a number of countries. However, interferon therapy has been reported to produce sustained clearance of hepatitis B e antigen (HBeAg) in 30–40% of North America and European patients, but only 25–65% of these patients ultimately cleared hepatitis B surface antigen (HBsAg). The response rate in Asian patients is lower: approximately 15–20% will clear HBeAg, of these only approximately 10% will clear HBsAg. One of the factors that affects the antiviral effects of these immunomodulatory agents is the high pretreatment HBV DNA level. Recently, second generation nucleoside analogs, such as lamivudine and famciclovir, have been shown to be effective in suppressing HBV replication with a good safety profile. However the nucleoside analogs have not been shown to maintain durable HBV DNA suppression once therapy is removed. Hence, the combination therapy goal is suppression and clearance.

There remains an urgent need in the art for effective anti-viral therapy against chronic HBV infection.

Thymosin alpha 1 (Tα1) initially isolated from Thymus Fraction 5 (TF5), has been sequenced and chemically synthesized. Tα1 is a 28 amino acid peptide with a molecular weight of 3108, which has shown activity similar to TF5 in modulating the maturation of T cells. Tα1 can influence immunoregulatory T cell function, promote interferon-alpha, interferon-gamma, and IL2 and IL3 production by normal human lymphocytes, and increase lymphocyte IL2 receptor expression.

There is evidence to suggest that Tα1 may influence recruitment of pre-NK cells, which would then become cytotoxic after exposure to interferon. Tα1 may also directly influence the lytic activity of mature NK cells. Recent investigations have shown that Tα1 enhances both allogenic and autologous human mixed lymphocyte reactions by activation of the T4 (helper/inducer)cells. This provides additional evidence that T4 cell may be the predominant target cell for the biological effect of Tα1.

Clinical trials of Tα1 as primary or adjunctive therapy for treatment of HBV infection indicate that it enhances immune responsiveness and augments specific lymphocyte parameters to significantly higher levels.

TF5 has been reported to decrease spontaneous cell-mediated lysis of hepatocytes using Peripheral Blood Mononuclear Cells (PBM) from patients with CHB. No effect on cytotoxicity was seen with TF5 treated control PBM. Additional studies showed that TF5 increased Con A-induced suppressor function in PBM from patients with CHB. Tα1 has been shown to enhance in vivo production of anti-HBs following Heptavax-B vaccination in previously non-reactive hemodialysis patients.

A controlled investigation was initiated in which 6 chronic woodchuck hepatitis virus (WHV)-carrier woodchucks were given twice weekly subcutaneous injections of Tα1 (10 µg/Kg) for 28 weeks. At the conclusion of the treatment, WHV DNA levels were undetectable in 4 of the treated animals, and were depressed 100-fold in the remaining 2 animals. Liver biopsy specimens obtained at the conclusion of treatment revealed a 50 to 300-fold decrease in the levels of WHV DNA replication intermediates in the 4 animals in which serum WHV DNA was undetectable-but only a small change from the pretreatment levels in the other 2 animals. No changes were identified in serum WHV DNA levels, or in tissue WHV DNA replication intermediates before or after treatment in any of the 6 untreated control animals.

In a US Phase II trial of Thymosin fraction 5 (TF5) and Thymosin alpha 1 (Tα1) in the treatment of CHB, 12 patients received TF5 or Tα1 and 8 patients received placebo twice weekly for six months. By the conclusion of the study (1 year), serum aminotransferase levels had improved significantly in the Thymosin e1-treated patients, but not in the placebo group. Nine (75%) of the Thymosin α1-treated patients and 2 (25%) patients given placebo cleared serum HBV DNA (p<0.004, Fisher's exact test). Response to Thymosin a1 therapy was associated with significant improvements in peripheral blood lymphocyte, CD3 and CD4 counts, and in vitro production of interferon-gamma over initial values. No side effects were observed in patients given Tα1, and several patients given TF5 experienced induration and erythema at the injection sites. About 78% of the responders had a sustained remission with normal ALT levels and negative serum HBV DNA (using PCR) and HBeAg.

Subsequently a U.S. Phase III CHB multi center, placebo controlled, double-blind study was conducted in 99 patients that were serum HBV DNA and HBeAg positive. All patients were HbsAg(+) for at least 6 months with persistent ALT elevation. Following a 3 month screening period, 50 patients were randomized to receive Tα1 (1.6 mg, S.C. 2x/week) and 49 to receive placebo (mannitol, NaPO4; S.C. 2x/week) for 6 months and followed at month intervals for 6 months. Thirty eight Tα1 treated patients and 32 patients given placebo were followed after the 1 yr study for 23+7 (SD) months respectively. Two patients were removed from the study after randomization but prior to treatment. Results are presented for 49 patients in the Tα1 group and 48 patients in the placebo group. There were no statistically significant differences in ALT values, HBV DNA levels and histological findings between the two groups at inclusion. A complete response (CR) to treatment was defined as a sustained serum HBV DNA(-) status (2 negative results at least 3 months apart) during the 1 year study with negative HBV DNA and HBeAg at 12 months. A delayed response (DR) was determined as a sustained HBV DNA(-) status achieved after 12 months with a negative HBV DNA and HBeAg at last assessment. An incomplete response (IR) was characterized as a sustained HBV DNA(-) status during the study or post study period with continued presence of HBeAg. The response to treatment was as follows:

| Group (n) | CR (%) | DR (%) | IR (%) |
|---|---|---|---|
| Tal(49) | 7(14%) | 5(10%) | 0(0%) |
| Placebo(48) | 2(4%) | 4(8%) | 2(4%) |
| p value | 0.084 | ns | ns |

A total of 12 (25%) patients treated with Tα1 and 6(13%) patients given placebo (p<0.11) showed a sustained loss of HBV DNA with negative HBeAg during the 1 yr study or post study follow up. Lamivudine is a reverse transcriptase inhibitor. As the activity of reverse transcriptase is necessary to transcribe the HBV-RNA pre-genome into HBV-DNA, a target for selective inhibition of viral replication is present. Selection of the negative enantiomer of 2'3'-dideoxy-3'-thiacytidine (lamivudine) enhances the antiviral activity but limits toxicity, probably because the negative enantiomer has difficulty in crossing the mitochondrial double membrane. The antiviral activity of lamivudine has been shown in HBV transfected cell lines, the duck model and in chronically infected chimpanzees. The drug has been used for up to 2 years in HIV-infected patients without significant toxicity.

Famciclovir is the oral form of penciclovir (BRL39123), a novel nucleoside analogue which has proven efficacy against the herpes simplex and zoster viruses. Famciclovir, the diacetylester of 6-deoxy penciclovir (asynthetic acyclic guanine derivative), is a prodrug of penciclovir (active component). Conversion to penciclovir takes place partly in the intestinal wall, where one ester group is removed, and is completed in the liver, where the remaining ester group is removed and oxidation occurs at the 6-position of the purine base.

Studies in volunteers have shown that famciclovir is well absorbed and produces penciclovir concentrations in the blood (Cmax 21.73 microgram/ml after a 500 mg oral famciclovir dose) superior to those obtained following oral administration of penciclovir alone (Cmax approximately 0.14 microgram/ml after a 5 mg/kg dose). Single and repeat doses of famciclovir have been given to human volunteers at daily doses up to 1000 mg three times daily for six days. There was no evidence of drug-related adverse effects on clinical laboratory values, blood pressure, heart rates or electrocardiograph (ECG) measurements.

An integrated safety evaluation involving 11 completed, randomized, double-blind clinical trials and 2 open trials (with more than 3000 patients tested) showed that the frequency of adverse experiences and laboratory abnormalities (hematology, clinical chemistry and urinalysis parameters) were similar in both famciclovir and placebo recipients. The most common adverse experiences were headache, nausea and diarrhea.

Penciclovir has been shown to be a potent inhibitor of HBV in human cells (2.2.15 hepatoma cells transfected with HBV genome). Activity in this in vitro system is said to correlate well with the activity of compounds against HBV when administered to chronic HBV carriers. Concentrations of penciclovir of 1 microgram/ml produced a 50% reduction in HBV DNA by 6 day and a 90% reduction by day 9. These effects were concentration dependent.

Penciclovir and famciclovir clearly inhibit duck hepatitis B viral replication in the Peking duck model. Both penciclovir (at oral doses of penciclovir of 20 and 100 mg/kg twice a day) and famciclovir (at oral doses of 5 and 25 mg/kg twice a day) reduced HBV DNA and DNA polymerase to undetectable levels within two days of the start of treatment, and maintained this suppression during the 21 days to treatment. Viral replication remained suppressed for at least two days after dosing had stopped, after which both HBV DNA and DNA polymerase levels returned to pre-treatment levels.

In a completed double-blind, placebo controlled, single centre pilot study in patients with chronic hepatitis B, a 10 day course of famciclovir (250 mg or 500 mg tid) resulted in a greater than 90% fall in HBV DNA levels in 6 of 11 evaluable patients. In an ongoing study in chronic hepatitis B, over 250 patients have received famciclovir at a dose of up to 500 mg three times a day for 16 weeks. Preliminary data from this study indicate that treatment with famciclovir resulted in a significant reduction in HBV DNA and ALT levels and was well tolerated with an adverse events profile similar to placebo. Famciclovir has also shown efficacy in a number of named patients with HBV reinfection following liver transplantation.

There remains a need in the art for improved methods of treating Hepatitis B.

SUMMARY OF THE INVENTION

In accordance with the present invention, treatment of hepatitis B virus (HBV) infection in a patient comprises administering to a patient in need of such treatment a drug regimen comprising an antiviral-effective amount of thymosin α1 (Tα1) and an antiviral-effective amount of lamivudine. In preferred embodiments, the drug regimen comprises thymosin $\alpha_{-1}$, lamivudine and famciclovir.

DESCRIPTION OF THE PREFERRED EMBODIMENTS

A novel modality for treating HBV infection in mammals has been devised, in which a drug regimen is administered to such mammals, the drug regimen including administration of antiviral-effective amounts of thymosin $\alpha_{-1}$ and administration of antiviral-effective amounts of lamivudine. In preferred embodiments, the drug regimen includes thymosin $\alpha_{-1}$, lamivudine and antiviral-effective amounts of famciclovir.

Separate dosage units of Tα1, lamivudine and optionally famciclovir, can be administered to the patient daily, one or more times per day, e.g., two or three times per day, and doses can be administered one or more days per week, e.g., two, three, four, five, six or seven days per week.

The terms "thymosin α1" and "Tα1" refer to peptides having the amino acid sequence disclosed in U.S. Pat. No. 4,079,137, the disclosure of which is incorporated herein by reference.

Antiviral-effective amounts of Tα1 are hepatitis B virus-reducing amounts of thymosin α1 which may be dosage units comprising about 0.5–10 mg of thymosin α1. Preferrably, the dosage unit comprises about 1–2 mg of Tα1. Most preferably, the dosage unit comprises about 1.6 mg of Tα1.

According to one aspect of this embodiment of the present invention, the dosage unit comprising Tα1 is administered to the patient on a routine basis. For example, the dosage unit can be administered more than once daily, once daily, weekly, monthly, etc. The dosage unit may be administered on a bi-weekly basis, i.e., twice a week, for example, on Tuesday and Saturday. Most preferably, the dosage unit of Tα1 is administered on a thrice weekly basis, i.e., three times per week.

According to another aspect of the invention, the administration of the dosage unit comprising Tα1 is administered for a period of time, concurrent with administration of lamivudine, sufficient to reduce or eliminate HBV infection in the patient.

Lamivudine, as noted above, is 2'3'-dideoxy-3'thiacytidine. According to preferred embodiments, dosage units comprising amounts of lamivudine which, in conjunction with administration of Tα1, are effective in reducing hepatitis B virus in a patient, are included within the dosage range of about 50–500 mg lamivudine. Preferred dosage units comprising lamivudine include about 100–200 mg lamivudine, most preferably about 150 mg lamivudine.

The dosage unit comprising lamivudine can be administered to the patient on a routine basis, for example, the dosage unit can be administered once daily, more than once daily (e.g., two, three or more times daily), weekly, monthly, etc. Most preferably, the dosage unit is administered once daily.

Administration of the lamivudine dosage unit can occur for a length of time, in conjunction with administration of Tα1, effective to reduce or eliminate HBV infection in the patient. Preferably, such administration occurs until HBeAg of the patient becomes negative, e.g., about 6–12 months.

In particularly preferred embodiments, Tol is administered by subcutaneous injection thrice weekly in pharmaceutical dosage units within the range of about 1–2 mg (e.g., about 1.6 mg). In conjunction with the administration to the patient of about 150 mg lamivudine orally, once daily.

According to another aspect of this embodiment, the administration of the dosage unit comprising Tα1 is administered for a period of time, concurrent with administration of lamivudine and famciclovir, sufficient to reduce or eliminate HBV infection in the patient.

Famciclovir, as noted above, is the diacetyl ester of 6-deoxypenciclovir. According to preferred embodiments, dosage units comprising amounts of famciclovir which, in conjunction with administration of Tα1, are effective in reducing hepatitis B virus in a patient, are included within the dosage range of about 100–2,000 mg famciclovir. Preferred dosage units comprising famciclovir include about 100–1,000 mg famciclovir, most preferably about 250 mg famciclovir.

The dosage unit comprising famciclovir can be administered to the patient on a routine basis, for example, the dosage unit can be administered once daily, more than once daily (e.g., two, three or more times daily), weekly, monthly, etc. Most preferably, the dosage unit is administered three times daily.

Administration of the famciclovir dosage unit can occur for a length of time, in conjunction with administration of thymosin α1, effective to reduce or eliminate HBV infection in the patient. Preferably, such administration occurs for at least about six months, and most preferably, for about 6–12 months.

In particularly preferred embodiments Tα1 is administered by subcutaneous injection twice weekly in pharmaceutical dosage units within the range of about 1–2 mg (e.g., about 1.6 mg), in conjunction with administration to the patient of about 150 mg lamivudine and 250 mg famciclovir orally, three times daily.

However, it is to be understood that pharmaceutical dosage units containing Tα1, lamivudine and famciclovir may be formulated in any suitable manner for administration by any suitable route.

The invention is applicable to native (i.e., naturally occurring Tα1 as well as synthetic Tα1 and recombinant Tα1 having the amino acid sequence of native Tα1, amino acid sequences substantially similar thereto, or an abbreviated sequence from thereof, and their biologically active analogs having substituted, deleted, elongated, replaced, or otherwise modified sequences which possess bioactivity substantially similar to that of Tα1.

The invention is applicable to lamivudine, analogs, homologs and derivatives thereof which possess bioactivity substantially similar to lamivudine, biologically active analogs which are capable of conversion to lamivudine or analogs, homologs or derivatives thereof which possess bioactivity substantially similar to lamivudine.

The invention is applicable to famciclovir, analogs, homologs and derivatives thereof which possess bioactivity substantially similar to famciclovir, biologically active analogs which are capable of conversion to penciclovir or analogs, homologs or derivatives thereof which possess bioactivity substantially similar to penciclovir.

The invention is also applicable to a pharmaceutical combination effective in treating hepatitis B virus infection in a patient, including a first dosage unit comprising an antiviral-effective amount of thymosin α1, a second dosage unit comprising an antiviral-effective amount of lamivudine and a third dosage unit comprising an antiviral-effective amount of famciclovir.

In preferred embodiments in which both lamivudine and famciclovir are utilized with Tα1 there is a lower probability for the HBV virus to mutate, thereby creating a low viral load period of long duration for the enhance immunological response of Tα1 to act.

Anti-viral agents such as nucleoside analogs are not viricidal, i.e., they do not kill viruses. They suppress the replication (reproduction) of the viruses so that the viral load goes down to unmeasurable levels. However, the viruses may not be eliminated altogether by nucleoside analogs alone.

Viruses, as replicating beings, have the propensity of changing their genetic material (DNA in the case of hepatitis B virus) during the replicative cycle by mutation. Under the pressure of a medication to suppress their replication, a virus may mutate into a strain which can withstand the action of the drug, and this tends to occur at a high rate.

If more than one drug is used at the same time, and if the drugs have different modes of action at the molecular level, a virus capable of surviving the suppressive action of both drugs would have to mutate simultaneously at two different points in its DNA. Simultaneous mutation at two different points is much more unlikely than a single mutation.

Thymosin $\alpha_{-1}$ is an immune system modulator that can play an instrumental role in the activation of host immunity mechanisms for the treatment of chronic hepatitis B.

Previous studies using Tα1 alone have only been partially satisfactory in patients where there is initially a very high viral load. Lamivudine, alone or in combination with famciclovir, prevents viral replication, thereby lowering the viral load and enhancing the effect of Tα1.

The invention is further illustrated by the following A examples, which are not intended to be limiting.

EXAMPLE 1

TREATMENT OF HEPATITIS B INFECTION IN HUMAN PATIENTS

Effacacy of hepatitis B treatment is shown by evaluating the biochemical (ALT), virological (HBV DNA), serological (HbeAg) and histological response in immune tolerant adult patients with chronic hepatitis B virus infection to treatment with Tα1 plus Lamivudine and optionally Famciclovir.

Efficacy Objectives

The primary endpoints will be the complete virological response rate defined as the percentage of patients with negative serum HBV DNA (as determined by the Chiron Quantiplex™ HBV DNA (bDNA) assay) and HBeAg at the end of 6-month treatment period and at the end of the 12-month follow-up period.

Safety Objectives

This study will evaluate safety data, including clinical status, hematological measures and measures of liver and kidney function, during the 6-month treatment period and for 12-month follow-up after the last administration of Tα1 plus Lamivudine and optionally Famciclovir.

Study Population

Criteria for Inclusion

1 Age$\geq$18 yrs and $\leq$65yrs.

2 Either male or female.

3 Documented evidence of the presence of HBsAg in the serum for at least six (6) months.

4 ALT<2.5 times the upper limit of normal on 2 determinations 4 weeks apart or the mean of 3 ALTs during the screening phase<2.5 times the upper limit of normal.

5 ALT<100 U/L during the screening phase. 6 HBV DNA>4,000 MEq/ml on 2 determinations>4 weeks apart. If the second HBV DNA determination is $\leq$4,000 MEq/ml, a 3rd determination must be done 4 weeks after the 2nd. The 3rd determination must be >4,000 MEq/ml (as determined by the Chiron Quantiplex (bDNA) assay).

7 Positive HBeAg on 2 determinations$\leq$4 weeks apart.

8 Liver biopsy within 12 months prior to enrolment consistent with chronic hepatitis.

9 Compensated liver disease with prothrombin time prolonged less than 5 sec over control, serum albumin$\geq$30 g/L, bilirubin$\leq$68 mmol/L.

10 Hematocrit$\geq$30%, platelet count$\geq$100×$10^9$/L, WBC$\leq$3.5×$10^9$/L, and polymorphonuclear white cell count$\leq$1.7×$10^9$/L.

11 Adequate renal function: calculated creatinine clearance$\leq$60 mL/min.

12 If a woman of child-bearing potential, use of an adequate method of contraception.

Criteria for Exclusion

1 Concomitant chronic use of any drug known to be hepatotoxic.

2 Concomitant chronic use of any immunosuppressive drug.

3 HIV infection diagnosed by HIV seropositivity and confirmed by Western blot.

4 Concomitant or prior history of malignancy other than curatively treated skin cancer or surgically cured in situ carcinoma of the cervix.

5 Active infectious process other than HBV that is not of a self-limiting nature. TB and AIDS are examples of infectious processes that are not of a self-limiting nature.

6 Cirrhosis.

7 A history of hepatic encephalopathy or bleeding esophageal varices.

8 Pregnancy documented by urine HCG pregnancy test.

9 Intravenous drug and alcohol abuse within the previous 5 years.

10 Patients who are poor medical or psychiatric risks or who have any non-malignant systemic disease that, in the opinion of the investigator, would make it unlikely that the patient could complete the protocol.

11 Simultaneous participation in another investigational drug study, or participation in any clinical trial involving experimental drugs within 30 days before study entry.

12 Any indication that the patient would not comply with the conditions of the study protocol.

13 Previous therapy with interferon or any other type of immunotherapy within 1 year of entry into the study or treatment with adrenocorticoid steroids within 6 months of entry into the study.

14 Any other liver disease including hepatitis C, hepatitis delta, alcoholic liver disease, drug-induced liver injury, primary biliary cirrhosis, sclerosing cholangitis, autoimmune hepatitis, hemochromatosis, α1 antitrypsin deficiency, or Wilson's disease.

15 Previous treatment with Tα1.

16 Previous treatment with Famciclovir.

17 Previous treatment with Lamivudine.

18 Patients with known hypersensitivity to Thymosin α1.

19 Patients with known hypersensitivity to Famciclovir.

20 Patients with known hypersensitivity to Lamivudine.

Conduct of Study

Screening Evaluation

All patients will undergo screening evaluation to determine eligibility for enrollment into the study. The evaluation consists of two, or on occasion three, separate screening visits. All data from screening visits will be recorded.

First Screening Visit (Screening Visit 1)

A. Eligibility

To be eligible for screening visit 1, the patient must have a history of chronic hepatitis as evidenced by a history of positive HBsAg for at least 6 months.

B. Screening Procedures

Laboratory screening tests at screening visit 1 will include HbsAg, HBeAg, hepatitis C antibody, hepatitis Delta antibody, HBV DNA, and ALT.

Complete history and physical examination.

Evaluate liver biopsy obtained within 12 months prior to enrolment.

Second Screening Visit

A. Eligibility

To be eligible to continue to screening visit 2, subjects must have positive HBsAg, HBeAg, and HBV DNA, and be negative for antibodies to hepatitis C and Delta.

B. Timing

Screening visit 2 will take place no less than 4 weeks after screening visit 1, and no more than 2 months after screening visit 1.

C. Screening Procedures

The following tests will be done at screening visit 2:
~Full blood count (FBC).Includes RBC, hematocrit, hemoglobin, WBC and differential counts
~Platelet count
~Prothrombin time (PT)
~Chemistry panel including BUN and creatinine
~ALT
~Serum albumin and total protein
~Bilirubin
~HbeAg
~HBV DNA
~anti-HIV
~Ferritin
~Antinuclear antibody
~α-fetoprotein
~Urine pregnancy test Third Screening Visit (Screening Visit 3)

A. Eligibility

A third screening visit will be required only if the value of HBV DNA at screening 2 is ≧4,000 MEq/ml or if 1 of the ALT values at 1st or 2nd Screening is >2.5 times the upper limit of normal, and the other is <2.5 times the upper limit of normal.

B. Timing

Screening visit 3, if required, will take place no less than 4 weeks and no more than 2 months after screening visit 2.

C. Procedures

Laboratory tests at screening visit 3 will include HBV DNA, HBeAg, and ALT.

Study Enrolment

Following the screening evaluation, patients will be reviewed to determine if they meet the inclusion and exclusion criteria.

After informed consent is obtained Patients will be started on treatment ≦4 weeks from the completion of the screening evaluation.

Treatment Phase

Patients will receive treatment with:
Tα1 1.6 mg SQ three times weekly (6 months).
Lamivudine 150 mg QD (once daily, 6 months).
Optionally Famciclovir 250 mg PO TID (three times daily, 6 months).
All subjects will have at least 12-months follow-up observation after completion of therapy.
Specific evaluations to be done during the treatment or observation portions of the study:
  Month 0. 1. 3. 6 during treatment then every 6 months for 12 months:
    HBV DNA
    HBeAg
    Anti-HBe(only if HBeAg is negative)
    HBsAg
    Polyclonal HBsAg (only if HBsAg turned negative by monoclonal test)
    Anti-HBc
    Anti-HBs (only if HBsAg is negative)
    Limited history and limited physical examination
    Chemistry panel including: ALT (SGPT), AST (SGOT), alkaline phosphatase, total bilirubin, BUN and creatinine.
    Hematology: RBC, hematocrit, WBC, differential, platelet count.
    Prothrombin time
    Urinalysis (specific gravity, glucose, protein, microscopic)
  At month 18:
    Repeat liver biopsy
    Only at Week 0: urine pregnancy test (postmenarchal female subjects only).
    Post-treatment Follow-up
    Post-treatment follow-up will continue for a minimum of 12 months as specified above, collecting the data listed.

Definition of Time Limits

When testing every four weeks is required, patients are expected to return for scheduled clinic examinations and testing within one week of the day specified in the protocol. Missed visits, or visits made more than one week before or after the scheduled day, will be treated as protocol violations but these patients will not be excluded from data analysis. When testing is scheduled at approximately three-month intervals, testing should be done within 3 weeks of the specified date.

Study Medication, Supplies, and Packaging

Dosage and Administration

The dose of Tα1 will be standardized at 1.6 mg per injection for all treated patients who weigh at least 40 Kg. Patients weighing less than 40 Kg will receive a dose of 40 ug/kg. This is based on the results of the phase II studies in which doses in the range of 1.45 to 1.75 mg (in adults) per twice-weekly injection were found to be safe and effective in clearing HBV DNA from the blood.

Lamivudine will be given at a dose of 150 mg once daily for all patients.

FAMVIR (Famicilovir) will optionally be given at a dose of 250 mg three times daily for six months.

Dosage Adjustments

No dosage adjustments are planned in this study.

Drug Supplies and Packaging

Synthetic Tα1, which has been formulated with mannitol and sodium phosphate, is manufactured by or for SciClone Pharmaceuticals in single-dose vials for injection. Vials will require reconstitution with sterile water for injection. The vials will be labelled with the drug name and dosage. This will be an open study.

Lamuvidine will be provided in 150 mg doses.

FAMVIR will be provided as 250 mg tablets.

All drug supplies must be kept in a secure area, and dispensed only by pharmacists or other research members designated by investigators who have been approved for participation in this study.

Concomitant Medications and Lifestyle Immunomodulatory drugs (except for the use of Tα1), glucocorticoids (such as prednisone), immunosuppressive drugs and drugs known to be hepatotoxic are prohibited.

No restrictions on other concomitant medications or lifestyle will be placed on the Patient; however, Patients will be discouraged from excessive use of alcoholic beverages.

Assessment of Compliance

Compliance with study medication dosing is defined as the Patient receiving ≧80% of the scheduled amount or study medication each month.

Patients will return to the clinic for each injection of Tα1, and administration of the dose will be documented by the person administering it. At the discretion of the investigator, a patient who is likely to be highly compliant with the protocol may make arrangements for home, or self administration.

In cases of home administration of drug the patient and/or the patient's parent(s) and, if so desired, a designated health care worker will receive instructions on the process of self-injection or assisted injection by the study nurse. The study nurse will continue to administer the investigational drug until assured of the patient's ability to self-administer, or of the ability of a parent of designated assistant to provide the injections. The study nurse will communicate with the patient or parent each week and record compliance with the injections. The patient or parent will maintain a diary of the injections actually given, and of any adverse experiences.

Patients having home injections will be given appropriate container for disposal of used needles and syringes, and instructed in proper disposal techniques.

Discharging Patients from the Study

Criteria for Discharging Patients

1. Any treated patient who has an adverse reaction to treatment that threatens his/her well being will have treatment discontinued. The patient will be monitored for resolution of the adverse event and will continue to be monitored on the protocol schedule until completing the study.

2. Any patient who demonstrates a significant deterioration in his/her clinical status, in hematological parameters, or in biochemical tests of liver and/or renal function will be evaluated by the investigator and the monitoring committee. Evidence that would suggest such a deterioration includes:
   a) Progressive increases in ALT or AST over an interval of 6 months. Note that transient elevations in ALT and AST may precede a treatment-related or spontaneous remission, and are not a reason for discharging the patient from the study.
   b) Progressive increases in the total serum bilirubin levels over an interval of 6 months.
   c) Subjective increase in symptomatology so as to preclude the same level of daily activity as exercised by the patient at the time of inclusion.
   d) Hematologic and renal parameters outside the ranges listed in the inclusion criteria.

3. Any patient who withdraws voluntarily from the study.

4. Failure of patient, for whatever reason, to comply with study medication dosing defined as the Patient receiving <80% of the scheduled amount or study medication each month or failure to comply with other requirements of the protocol.

5. Withdrawal from the treatment is considered by the investigator to be in the patient's best interest.

6. The patient dies during the study.

7. The patient has completed entire combined 6-month treatment and 12-month follow-up period.

Procedure for Handling Dropouts

Patients removed from this study because of noncompliance with study medication dosing, defined as the Patient receiving <80% of the scheduled amount or study medication each month, will be replaced.

All Patients removed from the study will continue to be followed, and their clinical course included in the final report.

Adverse Experiences

Documenting Adverse Experiences

Adverse event information will be documented during the entire combined 6-month treatment and 12-month follow-up period. Any adverse events continuing at the time of the last scheduled visit will be followed until they are resolved or explained or until the event stabilizes and the overall clinical outcome has been ascertained.

Patients will be monitored for significant side-effects or allergic manifestations possibly resulting from treatment. Although no local or systemic side effects have been observed with T$\alpha$1, the injections will be terminated if systemic hypersensitivity reactions such as urticaria or wheezing occur. Patients will be educated on the symptoms of severe anaphylactic reactions and informed of appropriate countermeasures.

All patients will be requested to report on any problems emerging since the previous visit. To avoid observer bias, all patients will be asked by non-directed questions about adverse events throughout the study. Non-directed questions include "Have you had any problems since your last visit?" When problems are described, they will be pursued in greater detail. The investigator will determine if the adverse event can reasonably be related to the study medication. All adverse events will be recorded, including date of onset, duration, and severity.

Assessment of Severity of Adverse Experiences

The severity of adverse events will be designated as mild, moderate, or severe as follows:

| | |
|---|---|
| Mild | No clinical significance, no requirement for additional assessment |
| Moderate | Event presented a problem, but did not affect daily activities or clinical status |
| Severe | Event resulted in marked alteration of daily activities or clinical status |

In addition to classifying the adverse event as mild, moderate, or severe the Investigator should determine whether or not an event is serious. The regulatory definition of a serious event includes those that are fatal, life-threatening (e.g., anaphylaxis), severely or prematurely disabling or incapacitating, or events resulting in or prolonging inpatient hospitalization, congenital anomaly, cancer, or a drug overdose (whether accidental or intentional).

Assessment of Causality

Every effort should be made by the investigator to explain each adverse experience and assess its relationship, if any, to study drug treatment. Causality should be assessed using the following categories: unrelated, probably related, possibly related, related.

The degree of certainty with which an adverse experiences is attributed to drug treatment (or alternative causes, e.g., natural history of the underlying diseases, concomitant therapy, etc) will be determined by how well the experience can be understood in terms of one or more of the following:
1. Known pharmacology of the drug.
2. Reaction of similar nature being previously observed with this drug or class of drug.
3. The experience having often been reported in literature for similar drugs as drug related e.g. skin rashes, blood dyscrasia.
4. The experience being related by time to drug ingestion terminating with drug withdrawal (dechallenge) or reproduced on rechallenge.

Follow-Up of Adverse Experiences

Investigators should follow-up subjects with adverse experiences until the event has subsided (disappeared) or until the condition has stabilized. Reports relative to the subject's subsequent course must be submitted to the clinical study monitor.

Overdose

Any instance of overdose (suspected or confirmed) must be communicated to the investigator within 24 hours and be fully documented as a serious adverse experience. Details of any signs or symptoms and their management should be recorded including details of any antidote(s) administered.

Pregnancy

Subjects who become pregnant during the study should discontinue treatment immediately.

Subjects should be instructed to notify the investigator if it is determined after completion of the study that they become pregnant either during treatment or within 30 days after the end of treatment.

Whenever possible a pregnancy should be followed to term, any premature terminations reported, and the status of the mother and child should be reported after delivery.

Administrative Requirements

Review and Consent Requirements

Ethical Review Committee

The sponsor will supply all necessary data to the investigator for submission to the Ethics Committee (Institutional Review Board) at the investigator's institution.

Ethics and Informed Consent

All patients will sign informed consent forms approved by the hospital Institution Review Board. The form will state the nature of the research study, the type of treatment options, the nature of samples to be obtained, and the possible risks and benefits. The investigator or his designee will obtain informed consent after ascertaining that the patient fully understand the contents of the consent form. A copy of the signed consent form will be given to the patient. Patient confidentiality will be maintained throughout the study, and patients will be identified on case report forms only by assigned study identification numbers.

Procedures and Possible Risks

Venipuncture and Phlebotomy

Patients will have approximately 30 ml of blood drawn prior to entry into the study, approximately monthly initially and every three months for the remainder of the study. For smaller patients, efforts will be made to draw only the minimum amount of blood required for the tests listed in this protocol. The blood loss resulting from this testing is not felt to be significant in the patients who will meet the criteria for inclusion in this study. Risk of venipuncture and phlebotomy will be minimized by use of an experienced person to carry out these procedures, and further minimized by use of aseptic technique.

Liver biopsy

Patients would have percutaneous liver biopsy performed before the entry into the study and at the end of the 12 months follow-up period. Liver biopsy would be performed by experienced hepatologist. The incidence of complications is less than 5% and this includes pain at the site of entry, hemorrhage, bile peritonitis, pneumothorax, penetration of abdominal viscera and sepsis. The mortality rate is less than 0.1%.

Laboratory

Laboratory studies will be conducted by a certified laboratory of the investigator's choosing. Investigators should employ the same laboratory during the entire study. The investigator will supply the sponsor with a copy of the laboratory's current certification, a list of the test methods used, and a list of normal ranges for the tests included in the protocol. When appropriate, normal values should be listed on age and sex. These must be provided at the onset of the study, and will be used to interpret results obtained in the study. If it is necessary to change laboratories during the study, or if the laboratory changes methodology or normal values, patient records must have the data of these changes noted. When possible, laboratory methods should not be changed during the course of the study.

For certain tests the sponsor may wish to specify a particular testing laboratory. For instance, determination of HBV DNA may be such a test. This will be negotiated with the investigator.

Data Evaluation

Criteria for Efficacy

Primary Endpoints

The primary endpoints will be the complete virological response rate defined as the percentage of the patients with negative HBV DNA (as determined by the Chiron Quantiplex™ HBV DNA (bDNA) assay) and HBeAg at the end of the 6-month treatment period and at the end of the 12-month follow-up period.

Secondary Endpoints

1. The percentage change from baseline in the levels of HBV DNA at the end of the 6-month treatment and 12-month follow up period;
2. The proportion of patients who have a reduction in their ALT levels to below the upper limit of the normal range at the end of treatment period and at the end of the 12 month follow up period;
3. The proportion of patients with loss of hepatitis B s antigen at the end of the treatment period and at the end of the 12 month follow up period;
4. The proportion of patients with an improvement in Knodell score of liver histology.

Safety Evaluation

The clinical assessments and frequent blood testing will provide a mechanism to monitor patients for drug safety and to minimize the risk of undiscovered adverse reactions.

Statistical Assessment

Analysis

Data will be analyzed by the investigators, and also by SciClone Pharmaceuticals, or by its statistical consultants. Data will be tested for normality, skewness, and heterogeneity of variances. If needed, data will be transformed using logarithmic function.

Analyses will include:

description and analyses of such demographic variables as age and sex baseline characteristics such as medical history and physical exam All significance testing will be done using two-tailed tests, and statistical significance will be based upon an alpha level of 0.05. Data listings, cross tabulations, and graphics will be used appropriately to support the analyses and the narrative report.

Safety Analysis

Safety assessment will be based upon analysis of observed clinical, local, or systemic effects. The incidence of abnormalities of each laboratory results will be presented. Laboratory abnormalities of individual patients will be reviewed by the medical monitor according to specified criteria.

Subgroup Analysis

The following subgroups will be identified, and their results analyzed. The results may not, depend upon the number of patients in each group, be statistically significant. In such instance, the information may be used as a guide to future studies:

1. Male patients; female patients
2. Liver biopsy
   patients showing minimal changes
   patients showing chronic persistent hepatitis
   patients showing chronic active hepatitis
3. Known duration of the patient's carrier state.
4. Patient age.

Example 2

Three adult patients (ages: 35–65) with chronic hepatitis B who are positive for HbeAg, HbeAg and HBV-DNA (50–250 pg/ml) and elevated ALT to at least twice normal (80–150 µ/l) were recruited to the study.

Treatment scheme: Tα1 1.6 mg thrice weekly for 6 months, plus lamivudine 150 mg once daily. The oral medication was continued until HBeAg became negative.

Results: All patients had normalization of ALT within three months of initiation of treatment. One year after iniation of therapy, all patients had normal ALT and were negative for HBV-DNA (hybrid capture). Two patients became negative for HBeAg while one remained HBeAg positive. All patients tolerated the treatment well and there were no serious side effects reported.

Example 3

The aim of this study was to investigate the efficacy of the combination of Tα1, which increases host immunity and lamivudine and famciclovir, which suppress viral replication.

Eleven patients with confirmed chronic hepatitis B and positive for HBsAg, HBeAg, and HBV DNA with an elevated ALT of at least two times normal were entered into the study. Tα1, 1.6 mg was administered SC thrice weekly for six months. Lamivudine, 150 mg QD and famciclovir 250 mg TID were administered until the patients became HBeAg negative.

Within one year of total treatment 64% (7/11) of the patients experienced a seroconversion of HBeAg to negative with all patients having the ALT normalize (11/11). The HBeAg seroconversion ranged in time from four to 11 months. The HBV DNA became negative in all patients. One patient experienced an ALT elevation of 150 U/L with continuation of therapy. However, this patient demonstrated a HBV DNA relapse. All of the patients tolerated the treatment and there were no serious side effects reported.

The combination of Tα1, lamivudine and famciclovir appears safe and effective in the treatment of chronic hepatitis B.

Positive results of the above study show effacacy of treatment of hepatitis B virus infection in patients with Tα1, lamivudine and optionally famciclovir.

Since many modifications, variations and changes in detail may be made to the described embodiment, it is intended that all matter in the foregoing description be interpreted as illustrative and not in a limiting sense.

What is claimed is:

1. A method of treating hepatitis B virus (HBV) infection in a patient, comprising administering to a patient in need of such treatment a drug regimen comprising an antiviral-effective amount of Thymosin alpha 1 (Tα1) and an antiviral-effective amount of lamivudine.

2. The method of claim 1 further comprising co-administering to said patient an anti-viral effective amount of famciclovir.

3. The method of claim 2 wherein said Tα1 is administered by injection in a dosage amount within the range of about 0.5–10 mg, said lamivudine is administered orally in a dosage amount within the range of about 50–500 mg and said famciclovir is administered orally in a dosage amount within the range of about 100–2,000 mg.

4. The method of claim 2 wherein said Tα1 is administered in a dosage amount within the range of about 1–2 mg, said lamivudine is administered orally in a dosage amount within the range of about 100–200 mg and said famciclovir is administered in a dosage amount within the range of about 250–1,000 mg.

5. The method of claim 4 wherein said Tα1 is administered to said patient thrice weekly, said lamivudine is administered to said patient once daily and said famciclovir is administered to said patient three times daily.

6. The method of claim 4 wherein said Tα1 is administered in a dosage amount of about 1.6 mg, said lamivudine is administered in a dosage amount of about 150 mg and said famciclovir is administered in a dosage amount of about 250 mg.

7. The method of claim 6 wherein said Tα1 is administered to said patient thrice weekly, said lamivudine is administered to said patient once daily and said famciclovir is administered to said patient three times daily.

8. A pharmaceutical combination for use in treating hepatitis B virus (HBV) infection in a patient, including a first dosage unit comprising an antiviral-effective amount of thymosin alpha 1 (Tα1) and a second dosage unit comprising an antiviral-effective amount of lamivudine.

9. The combination of claim 8 further comprising a third dosage unit comprising an antiviral-effective amount of famciclovir.

10. The combination of claim 9 wherein said dosage unit of Tα1 is a dosage amount within the range of about 0.5–10 mg, said dosage unit of lamivudine is a dosage amount within the range of about 50–500 mg and said dosage unit of famciclovir is a dosage amount within the range of about 100–2,000 mg.

11. The combination of claim 9 wherein said dosage unit of Tα1 is a dosage amount within the range of about 1–2 mg, said dosage unit of lamivudine is a dosage amount within the range of about 100–200 mg and said dosage unit of famciclovir is a dosage amount within the range of about 100–1,000 mg.

12. The combination of claim 9 wherein said dosage unit of Tα1 is a dosage amount of about 1.6 mg, said dosage unit of lamivudine is a dosage amount of about 150 mg and said dosage unit of famciclovir is a dosage amount of about 250 mg.

13. The method of claim 1 wherein said $T\alpha_{-1}$ is administered by injection in a dosage amount within the range of about 0.5–10 mg, and said lamivudine is administered orally in a dosage amount within the range of about 50–500 mg.

14. The method of claim 13 wherein said $T\alpha_{-1}$ is administered in a dosage amount of about 1.6 mg, and said lamivudine is administered in a dosage amount of about 150 mg.

15. The method of claim 14 wherein said $T\alpha_{-1}$ is administered to said patient twice weekly, and said lamivudine is administered to said patient once daily.

16. The combination of claim 8, wherein said dosage unit of $T\alpha_{-1}$ is a dosage amount within the range of about 0.5–10 mg, and said dosage unit of lamivudine is a dosage amount within the range of about 50–500 mg.

17. The combination of claim 8, wherein said dosage unit of $T\alpha_{-1}$ is a dosage amount of about 1.6 mg, and said dosage unit of lamivudine is a dosage unit of about 150 mg.

* * * * *